United States Patent [19]

Landa et al.

[11] Patent Number: 5,210,590
[45] Date of Patent: May 11, 1993

[54] RAPID SCANNING SPECTROGRAPHIC ANALYZER

[75] Inventors: Isaac J. Landa, Potomac; Michael M. Anthony, Gaithersburg, both of Md.

[73] Assignee: L. T. Industries, Inc., Rockville, Md.

[21] Appl. No.: 836,403

[22] Filed: Feb. 18, 1992

[51] Int. Cl.⁵ .................. G01J 3/08; G01J 3/18; G01J 3/42
[52] U.S. Cl. .................. 356/319; 356/323; 356/328
[58] Field of Search .............. 356/319, 323, 325, 326, 356/328, 434, 436; 250/227.11

[56] References Cited

U.S. PATENT DOCUMENTS

| | | | |
|---|---|---|---|
| 3,697,185 | 10/1972 | Kassel et al. | 356/410 |
| 3,861,788 | 1/1975 | Webster . | |
| 4,264,205 | 4/1981 | Landa | 356/326 |
| 4,285,596 | 8/1981 | Landa | 356/308 |
| 4,529,308 | 7/1985 | Rife | 356/323 |
| 4,540,282 | 9/1985 | Landa et al. | 356/328 |
| 4,594,533 | 6/1986 | Snook et al. | 250/363 |
| 4,630,255 | 12/1986 | Gouali et al. . | |
| 4,669,817 | 6/1987 | Mori . | |
| 4,685,801 | 8/1987 | Minekane | 356/328 |
| 4,820,045 | 4/1989 | Boisde et al. | 356/319 |
| 4,848,871 | 7/1989 | Seidel et al. . | |
| 4,989,932 | 2/1991 | Landa et al. | 356/300 |
| 5,020,909 | 6/1991 | Landa | 356/440 |
| 5,044,755 | 9/1991 | Landa et al. | 356/440 |
| 5,131,746 | 7/1992 | O'Rourke et al. | 356/319 |

OTHER PUBLICATIONS

Landa, "High Energy Spectrophotometer for Rapid Constituent Analysis in the Range of 0.25-2.4 μm", Rev. Sci. Instrum., vol. 50, No. 1, Jan. 1979, pp. 34-40.

*Primary Examiner*—F. L. Evans
*Attorney, Agent, or Firm*—Sterne, Kessler, Goldstein & Fox

[57] ABSTRACT

An fixed grating, detector-array type analyzer rapidly multiplexes multiple channels. The analyzer comprises a light source, a detector array-type spectrograph, and an optical multiplexer. The multiplexer can select from one of a plurality of channels. Further, the multiplexer can convolute light passing through it with a reference spectrum for calibration and wavelength drift compensation. Rapid multiplexing is achieved using a fiber optic slit array which "perpendicularly multiplexes" the plurality of channels.

14 Claims, 11 Drawing Sheets

RAPID SCANNING SPECTROGRAPHIC ANALYZER

FIELD OF THE INVENTION

The present invention relates generally to the field of spectroscopy. That is, the invention relates to the field of instruments for spectrally measuring and analyzing the optical properties of samples.

BACKGROUND OF THE INVENTION

Spectroscopy is a branch of physics which is concerned with the production, measurement, and interpretation of electromagnetic spectra arising from either emission or absorption of radiant energy by various substances. Essentially, a beam of polychromatic light is directed to a sample. The light transmitted through the sample, reflected from the sample, or both is then collected and analyzed. Analysis involves separating the collected light into its individual wavelengths and then determining the energy content at each wavelength. Because a sample will absorb certain wavelengths of light more than others, the collected light has a spectrum which is indicative of the composition of the sample.

Because spectroscopy can rapidly provide accurate composition analysis, it has found a wide variety of applications. For example, in the areas of food and agriculture, spectrometers are used for the measurements of constituents in dairy products, cereal, grains, beverages, fruits, meats, etc. Other examples of applications for spectroscopic analyzers include:

- measuring lubrication of yarn and for fiber finish in nylon, polyester, cotton and others in the textile industry;
- measuring the percent of tar and nicotine in the tobacco industry;
- chemical analysis of paper including colorings, thickness, and moisture in the paper industry;
- measuring tape and film thicknesses in the plastics industry;
- compositions determination in the gasohol and petroleum industry;
- measurement of the content of oils and other ingredients in the cosmetics and perfume industry; and
- measurement and identification of drug composition in the pharmaceutical industry.

There are various types of spectral analyzers on the market for performing these types of analysis, including the moving grating analyzer and the fixed grating, detector array-type analyzer. The moving grating analyzer provides highly accurate spectral data and is best suited for applications where accuracy is paramount. These devices are capable of scan/sample rates up to a few scans per second. U.S. Pat. No. 4,540,282 to Landa et al. discloses one such scanning analyzer.

For applications (e.g., product sorting) where speed is paramount, the fixed grating, detector array-type analyzer is most suitable. Fixed grating analyzers are capable of scan rates in excess of 100 scans per second. The conventional fixed grating analyzers includes a light source, an optical probe or a sample chamber, and a spectrograph. The analyzer is normally a single channel device. That is, only a single probe is used such that the analyzer can only be used for a single application at any one time.

Because spectral analyzers tend to be expensive, it is desirable to produce a multiple channel analyzer. Multiple channels would allow a single analyzer to be simultaneously used for numerous measurements and applications. In order to handle multiple channels, the analyzer must time multiplex the spectral data which is provided to the spectrograph. Unfortunately, conventional optical multiplexing schemes have tended to be inaccurate and slow such that the very forte of the analyzer is sacrificed for the added channels.

SUMMARY OF THE INVENTION

The invention is a rapid scanning, multi-channel, fixed grating, visible through NIR (near infrared) analyzer which is capable of a scan/sample rate (hereinafter, "scan rate") in excess of one hundred scans per second. This scan rate is achieved in a multi-channel analyzer by using a unique multiplexing scheme. Both high resolution and high accuracy are maintained using an "inline" reference method of calibration and wavelength drift compensation.

The analyzer comprises a light source; a fixed grating, detector array-type spectrograph; and an optical multiplexer. The multiplexer can select from one of a plurality of channels. Further, the multiplexer implements the "in-line" reference method by selectively convoluting light passing through it with a reference spectrum, blocking all light, or providing the light from the light source directly to the spectrograph; each for calibration and wavelength drift compensation. Rapid multiplexing is achieved using a fiber optic slit array which consists of "perpendiculary multiplexed" channels of optical fibers.

DESCRIPTION OF THE PREFERRED EMBODIMENT

The invention is a rapid scanning visible through NIR (near infrared) analyzer which is capable of scan/samples rates (hereinafter, "scan rate") in excess of one hundred scans per second. This scan rate is achieved using a unique multiplexing scheme. Both high resolution and high accuracy are maintained using an "in-line" reference method of spectral compensation.

Figure 1:
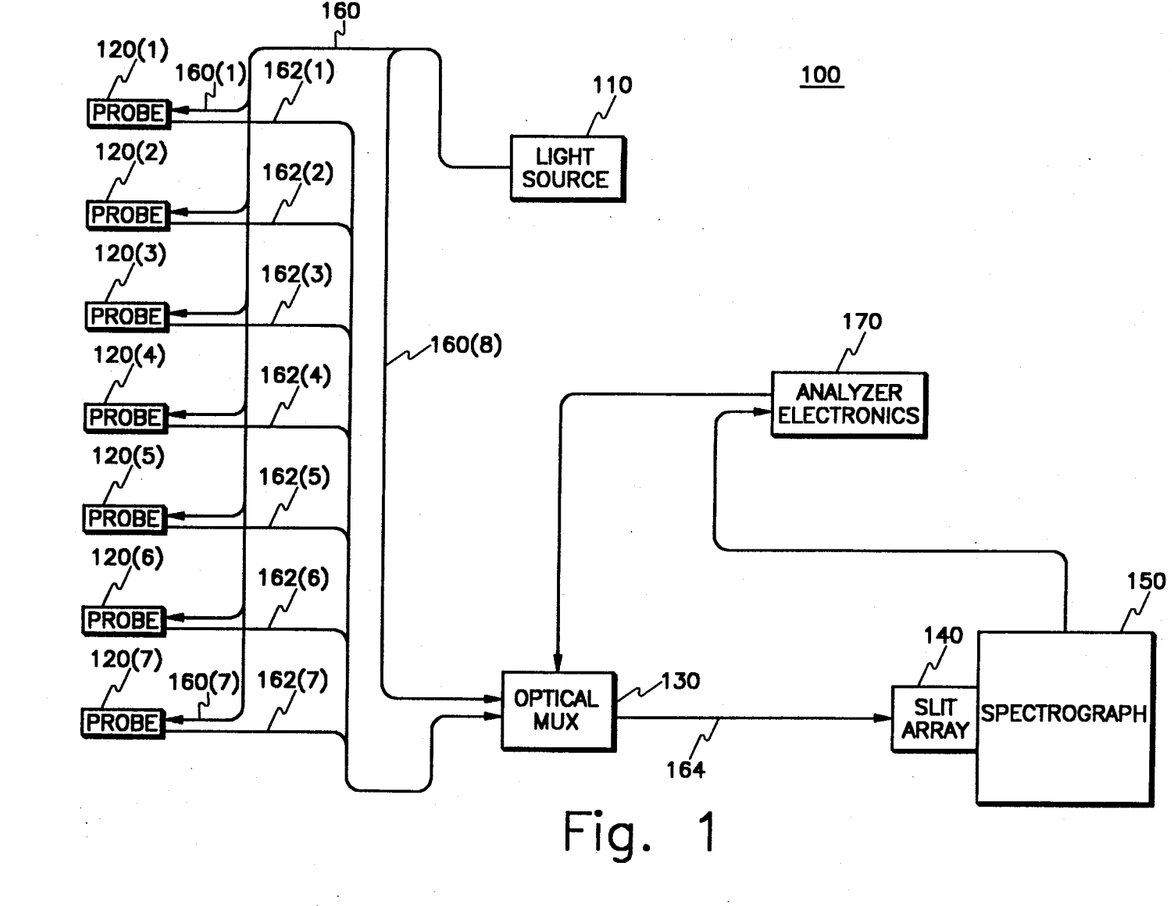
FIG. 1 is a block diagram of the analyzer of the present invention.

A block diagram of the preferred embodiment of the invention is shown is FIG. 1. Analyzer 100 includes a light source 110, a plurality of optical probes 120, an optical multiplexer (MUX) 130, a fiber optic slit array 140, a spectrograph 150, and analyzer electronics 170. Light source 110 provides light to each of probes 120 via optical fibers 160. Light is also provided directly to MUX 130 via optical fibers 160. Each optical probe 120 directs the light unto a sample. The light which is reflected from a sample, passed through a sample, or both, is then collected and routed to MUX 130 via optical fibers 162. Collection of the light from the sample may be performed by the same probe or by an additional collection probe as discussed below.

MUX 130 selects the light from a single sample or from reference fibers 160(8) and then directs the selected light sample to slit array 140 over optical fibers 164. Slit array 140 transmits the light into spectrograph 150 for analysis.

Analyzer electronics 170 receives the spectral information from spectrograph 150 in the form of an electrical signal, digitizes the signal, and then analyzes it.

The preferred embodiment of analyzer 100 is an eight channel device. Thus, seven optical probes 120 are shown and optical multiplexer 130 is capable of a seven-to-one multiplexing ratio. Only seven probes are used because light from source 110 is routed directly to the eighth channel of MUX 130 to act as a light reference (described below). Including the light reference channel, MUX 130 is capable of an eight-to-one multiplexing ratio.

It should be understood that eight channels were selected as a design choice capable of meeting the requirements of many applications. Analyzer 100 may be designed with any number of channels as desired. In fact, a sixteen channel device is also contemplated for production along with the eight channel preferred embodiment.

Optical Fibers

Optical fibers 160 includes eight optical fiber bundles 160(1)-160(8). Fiber bundles 160(1)-160(7) carry light to optical probes 120. Fiber bundle 160(8) carries light directly to MUX 130. Optical fibers 162 includes seven optical fiber bundles 162(1)-162(7). Optical fiber bundles 162(1)-162(7) carry light from probes 120(1)-120(7) and deliver it to MUX 130. Optical fibers 164 includes eight optical fiber bundles 164(1)-164(8).

Each optical fiber bundle carries light for a single channel. For example, light from source 110 is transmitted to probe 120(1) over fiber bundle 160(1), from probe 120(1) to MUX 130 over fiber bundle 162(1), and from MUX 130 to slit array 140 over fiber bundle 164(1). Each fiber bundle may consist of a single optical fiber or a plurality of optical fibers. Each fiber is capable of transmitting a certain amount of light energy. Therefore, increasing the number of fibers will increase the amount of light energy available for analysis. In the currently preferred embodiment, each fiber bundle includes a single optical fiber. The inventors, however, contemplate using multiple fibers (e.g., five) per bundle in future analyzers.

On the source end, when multiple fibers are used in a bundle, it is desirable to ensure that each fiber transmits light having similar spectra. This, however, does not occur as a matter of course. Light is directed into the individual fibers by placing their ends near the filament of the light source. Imperfections in the filament, however, cause different portions of the filament to produce light with varying spectral contents. Therefore, it is desirable for every fiber of a fiber bundle to "look" at the same portion of the filament.

Figure 2:
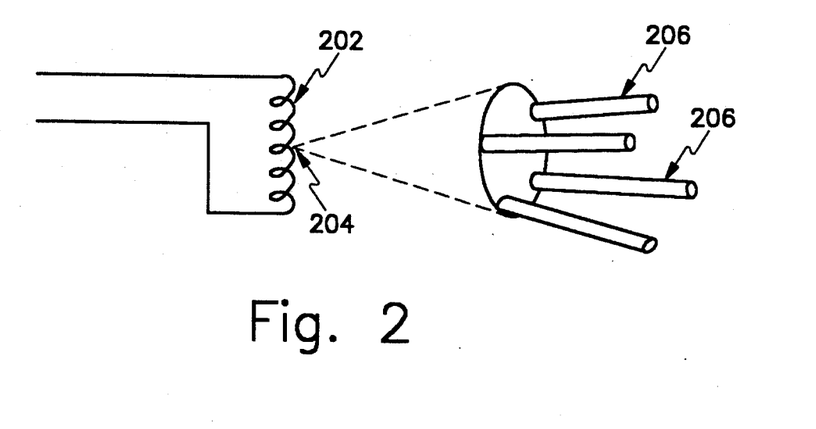
FIG. 2 is a schematic diagram illustrating the relationship between the filament of light source 110 and the ends of optical fibers 160.

This is accomplished by arranging the end of each fiber of the fiber bundle around a filament in a conical pattern as shown in FIG. 2. A sample filament 202 having portion 204 is shown. A plurality of fibers 206 are arranged in a conical pattern such that the end of each fiber 206 is linearly aligned with point 204 of filament 202. This allows light emitted from portion 204 of filament 202 to fall directly incident on the ends of fibers 206.

As an alternative to optical fibers, optical waveguides could be used for optical fibers 160, 162, and 164.

Light Source 110

Light source 110 is a polychromatic light source which has a predetermined wavelength spectrum. Any type of light source may be used which emits broadband light in the desired spectral range with sufficient intensity. The preferred spectral range is visible through NIR which corresponds to the wavelengths 400-2400 nm. However, any range over the wavelength region that corresponds to ultraviolet (UV), through visible, through NIR, and up to infrared (IR) may be used. In the preferred embodiment, a tungsten halogen lamp, which produces light in the visible through NIR range, is used for light source 110.

Optical Probes 120

A variety of optical probes may be used for optical probe 120, depending on the specific application. There are basically three modes by which a probe may operate. These include reflectance, transmittance, and transflectance. In the reflectance mode, light is introduced onto a sample via the probe tip. Light is then reflected back to the probe for collection and analysis. Generally, this type of probe will have a bi-directional optical fiber arrangement which enables light to move in two directions through the probe.

In the transmittance mode, a first probe introduces light through the sample and a second probe receives the light which has been transmitted through the sample. Normally, this mode requires two probes: one for transmitting the light and one for collecting the light.

The transflectance mode is similar to the reflectance mode in that a bidirectional fiber is generally used to both transmit light to and receive light from the sample. In this mode, light is introduced to the sample. Light which is reflected from the sample is returned to the probe and transmitted back for analysis. Light which transmits through the sample is reflected back through the sample by a mirror, and again through the probe for analysis. U.S. Pat. No. 5,044,755 to Landa et al., the disclosure of which is incorporated herein by reference, provides an example of a transflectance type probe.

The particular probe used with analyzer 100 will depend on the requirements of the samples being analyzed. Reflectance, transmittance, and transflectance type probes are known in the art. For ease of discussion, a reflectance type probe is selected for each of probes 120.

Figure 3:
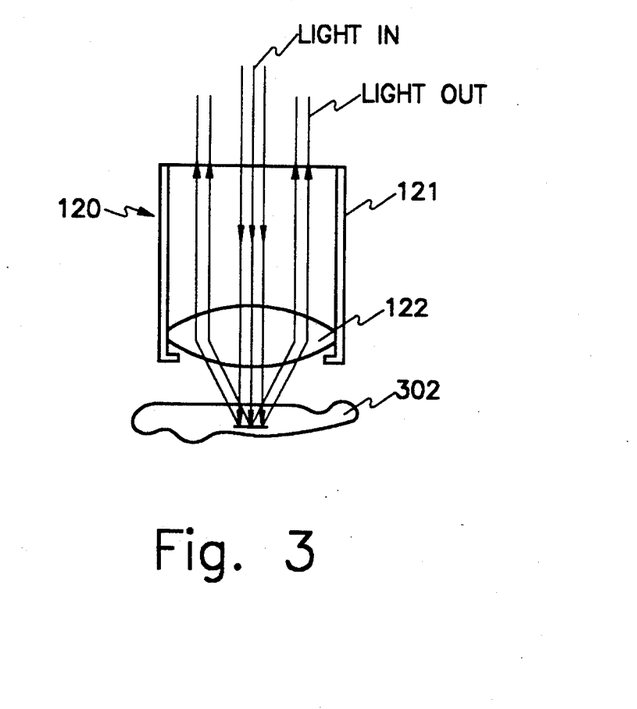
FIG. 3 is a simplified cross-sectional view of a reflectance-type optical probe.

A sample reflectance probe 120 is shown in FIG. 3. Probe 120 includes a probe body 121 and a collimating lens 122. Light from light source 110 (via optical fibers 160) enters probe body 121 and is directed unto a sample 302 by lens 122. Light reflected from sample 302 is then collected by lens 122 and directed back up through probe body 121 to optical fibers 162.

Optical Multiplexer 130

Optical multiplexer (MUX) 130 is a multi-channel spacial array MUX for selectively distributing light from several fiber-optic point sources into the input of spectrograph 150. MUX 130 is shown in detail in FIGS. 4 and 5. MUX 130 includes an input disk 131, a chopping disk 132, an output disk 133, and a stepper motor 134. Disks 131 and 133 are maintained in fixed positions centered about an axis 135. Chopping disk 132 is rotatable about axis 135 by stepper motor 134.

Figure 4:
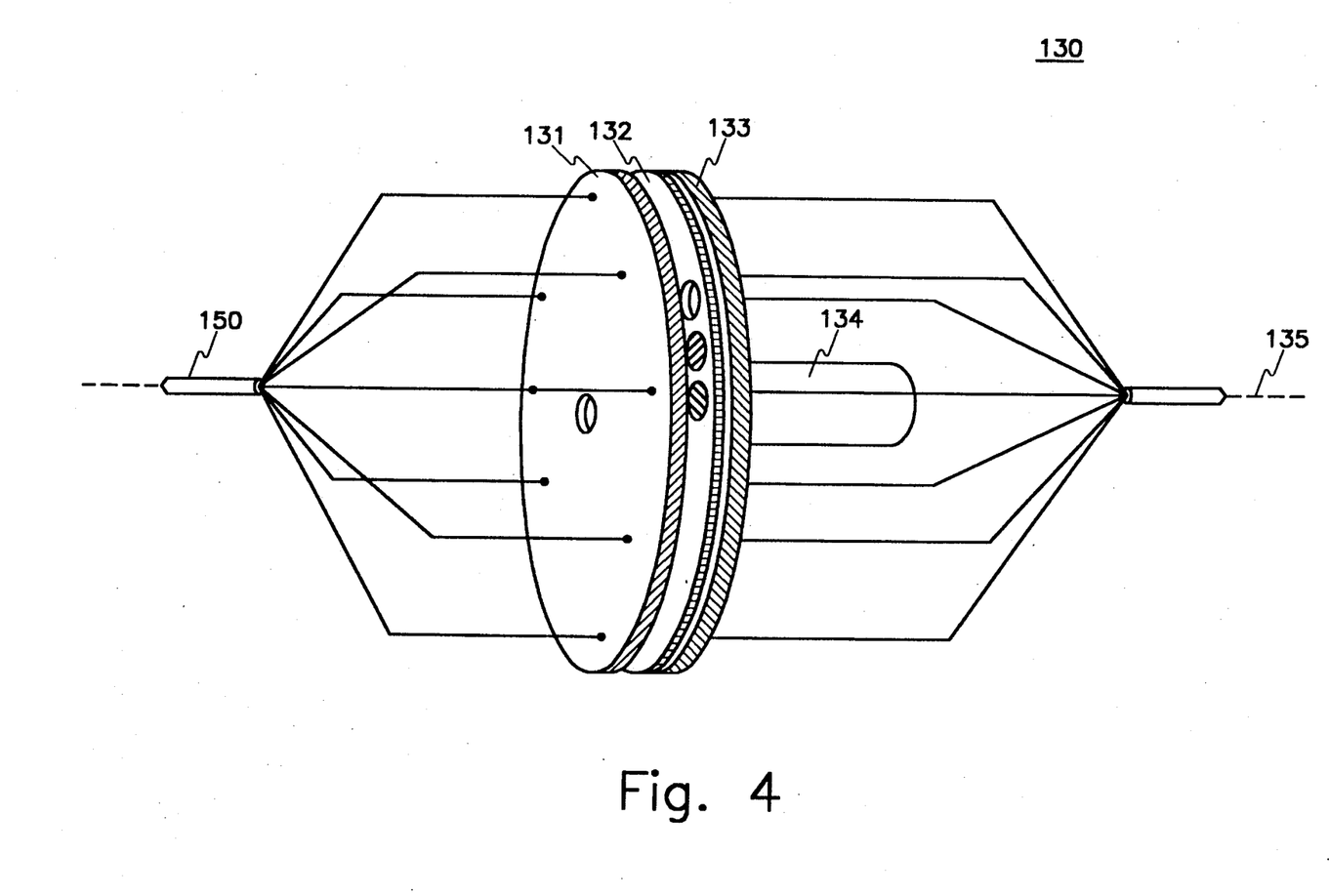
FIG. 4 is a simplified perspective view of multiplexer 130.
Figure 5:
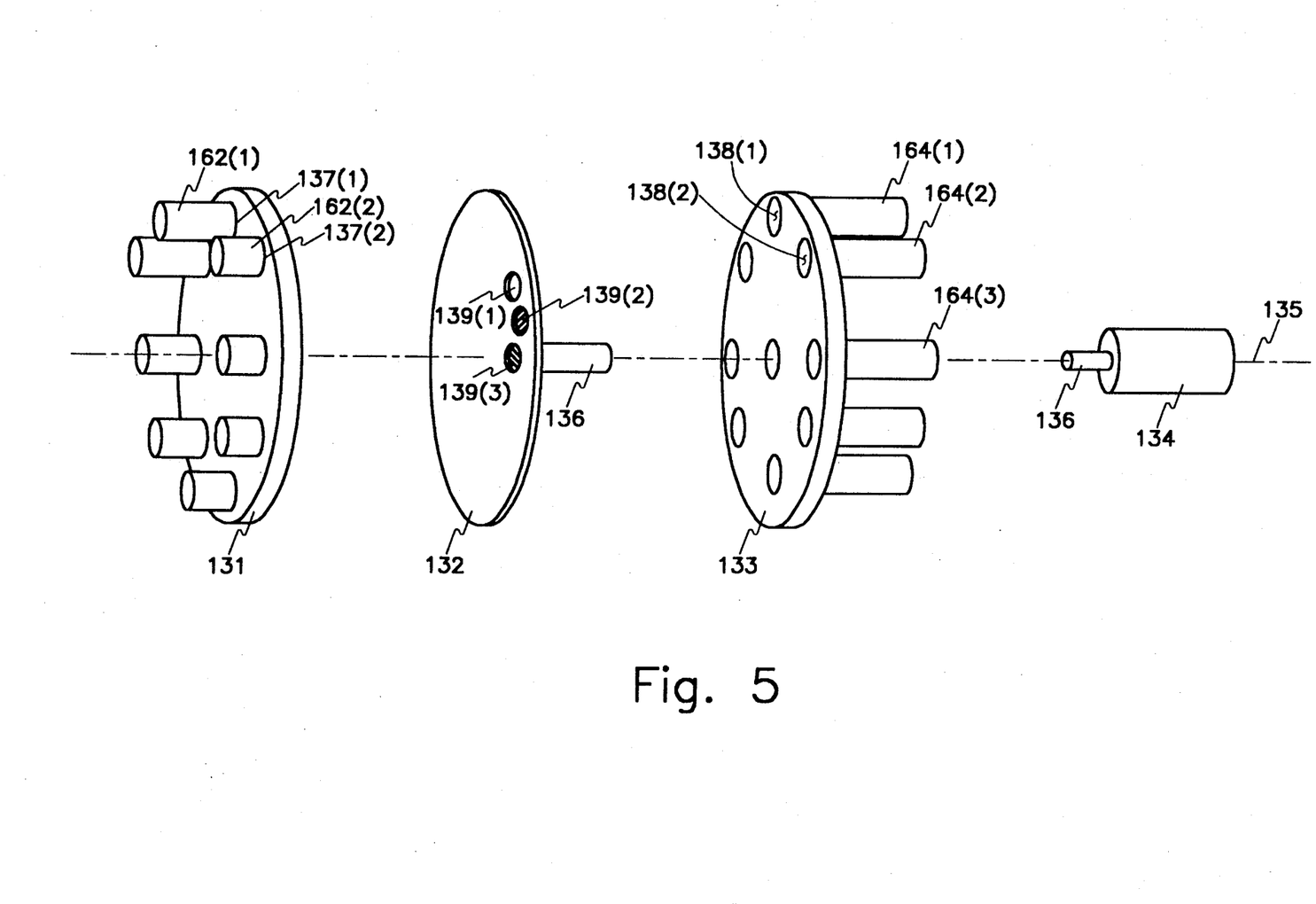
FIG. 5 is an exploded diagram of multiplexer 130.

Input disk 131 has a plurality of openings 137 equally spaced about its periphery. In the preferred embodiment, there are eight openings 137(1)-137(8) in disk 131 to correspond to each of the eight channels. Each opening 137 is adapted to interface with a corresponding fiber bundle 162. For example, fiber bundle 162(1) interfaces with opening 137(1). Each opening 137 contains a collimating lens (not shown) to collimate the light from fiber bundles 162.

Output disk 133 is shaped identically to input disk 131. Output disk 133 has a plurality of openings 138 equally spaced about its periphery. There are eight openings 138(1)-138(8) in disk 131 to correspond to each of openings 137(1)-137(8). Each opening 138 is adapted to interface with a corresponding fiber bundle 164. For example, fiber bundle 164(1) interfaces with opening 138(1). Each opening 138 contains a focusing lens (not shown) to collect light incident upon it and to deliver it to optical fibers 164.

Figure 6:
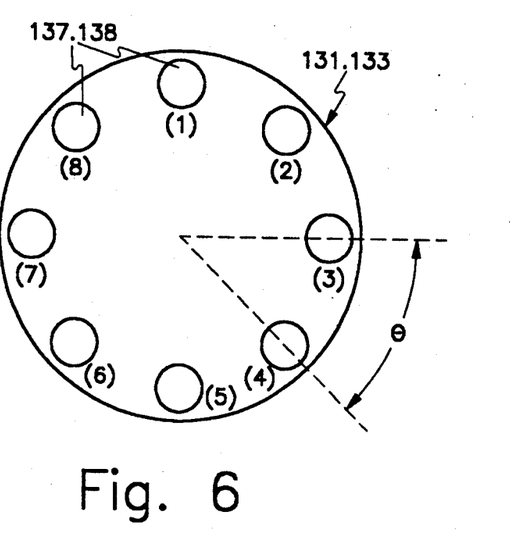
FIG. 6 is a top view of either of input disk 131 or output disk 133 of multiplexer 130.

FIG. 6 is a frontal view of either of input disk 131 or output disk 133. As can be seen, openings 137,138 are equally spaced around the periphery of the disk such that the angle $\theta$ between adjacent openings is 45° (i.e., 360° divided by 8 openings). Input disk 131 and output disk 133 are positioned such that each opening 137 of disk 131 is lined up to correspond to an opening 138 of disk 133. This will allow light passing out of opening 137(1), for example, to be coincident on and collected by opening 138(1).

Figure 7:
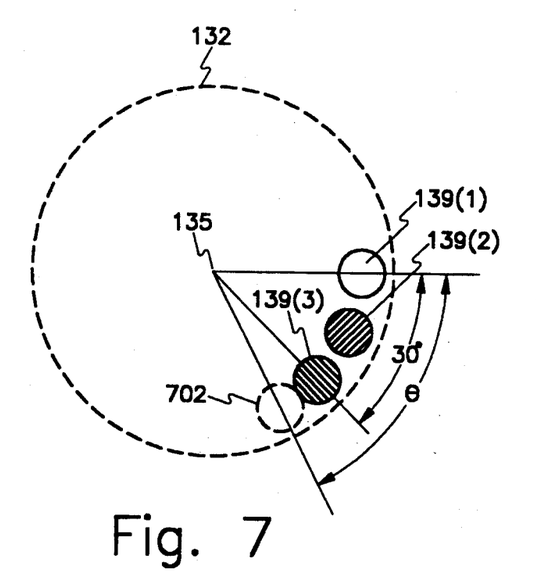
FIG. 7 is a top view of chopper disk 132 multiplexer 130.

Chopping disk 132 is shown in FIG. 7. Disk 132 is constructed from an opaque material such that light will not pass through it. It, however, has three openings 139 disposed at its periphery. A first opening 139(1) is empty and provides merely an air gap to light passing therethrough. A second opening 139(2) is filled with a transparent reference material which is described in greater detail below. A third opening 139(3) is filled with an opaque material. Alternatively, third opening 139(3) may be omitted, and the opaque material from which disk 132 is constructed may act as the opaque material filling third opening 139(3).

Chopping disk 132 is disposed between input disk 131 and output disk 133. While disks 131 and 133 are stationary, chopping disk 132 is rotated about axis 135 by stepper motor 134. A shaft 136 of stepper motor 134 passes through output disk 133 (or input disk 131 depending on the position of stepper motor 134) and is attached to chopping disk 132 for imparting rotational motion thereto.

When input disk 131, chopping disk 132, and output disk 133 are properly aligned, each opening 137 will align with a corresponding opening 138 to form an opening pair 137,138. Openings 139 are arranged on chopping disk 132 such that only one of openings 139 may align with an opening pair 137,138 at a time. Disk 132 will block light transmission between all other opening pairs 137,138. This is accomplished by assuring that all three of openings 139 are disposed within 30° of arc as shown in FIG. 7. For example, if opening 139(1) (i.e., air) is aligned with opening pair 137(3),138(3), then all other opening pairs 137,138 will be blocked. A phantom circle 702 indicates the location of opening pair 137(4),138(4) when disks 131-133 are aligned in this fashion. By stepping chopping disk 132 15° in a counter-clockwise direction, opening 139(2) (i.e., reference material) is brought into alignment with opening pair 137(3),138(3). By stepping chopping disk 132 an additional 15° in a counter-clockwise direction, opening 139(3) (i.e., an opaque material) is brought into alignment with opening pair 137(3),138(3). This is equivalent to blocking all opening pairs such that no light is passed through chopping disk 132.

In this manner, MUX 130 will allow only one of fiber bundles 162 or fiber bundle 160(8) (connected to input disk 131) to transmit light to a corresponding fiber bundle 164 (connected to output disk 133). Further, the light from each bundle may be passed through an air gap [i.e., opening 139(1)], a reference material [i.e., opening 139(2)], or blocked completely by an opaque material [i.e., opening 139(3)]. These three alternatives are used for spectral calibration and wavelength drift compensation as described in detail below.

In order to keep track of which channel of MUX 130 is active, it is necessary to keep track of the position of chopping disk 132. To accomplish this, the position of multiplexer disk 132 must be initialized periodically (e.g., at power up) to determine a "home" position. The active channel can then be determined by counting the number of steps of rotation which have been made from the "home" position. This can be accomplished by the analyzer electronics 170. The "home" position can be determined by providing a small locator hole, notch, or reflective substance (not shown) on chopping disk 132 which can be sensed by an optical sensor (not shown). The optical sensor could then provide a "home" signal to the analyzer electronics 170.

Spectrograph 150

Spectrograph 150 is the core component of analyzer 100. The essential components of a spectrograph are an entrance slit, a diffraction grating, and a device to record the produced spectrum of wavelengths.

Figure 8:
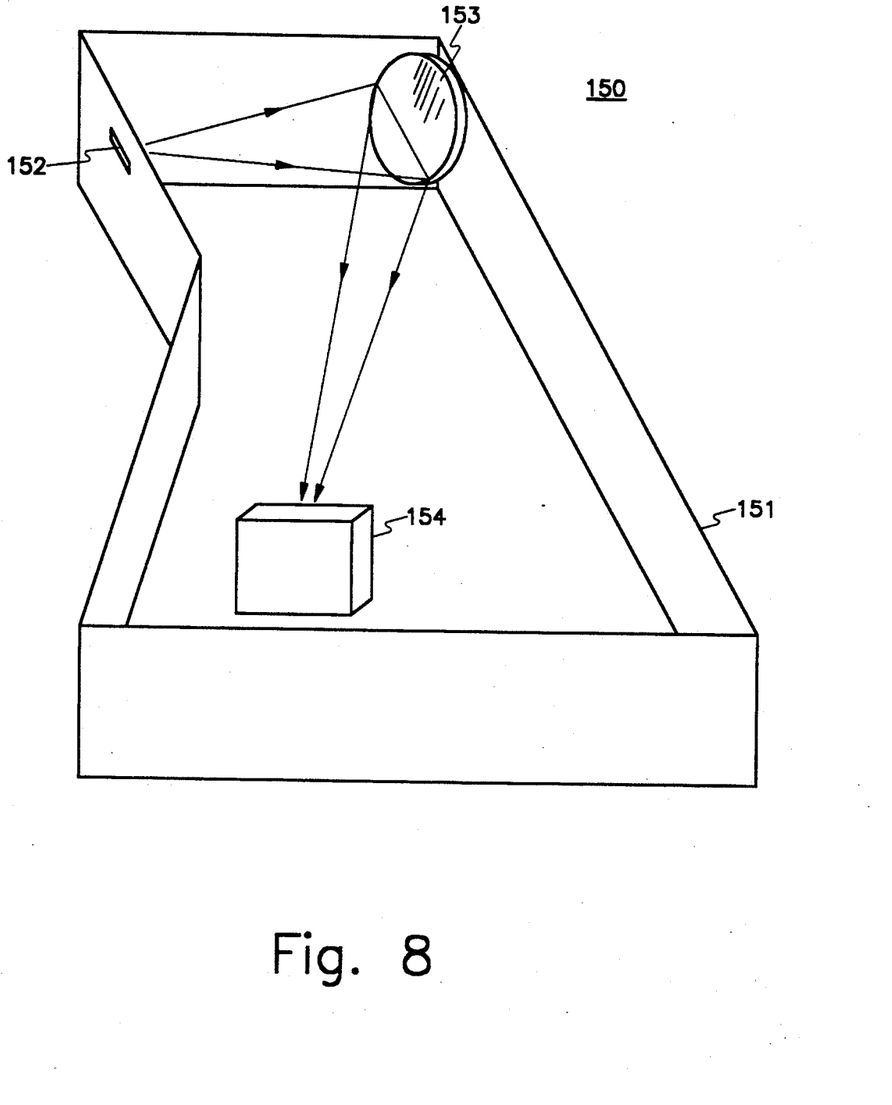
FIG. 8 is a simplified, perspective view of a detector array-type spectrograph.
Figure 9:
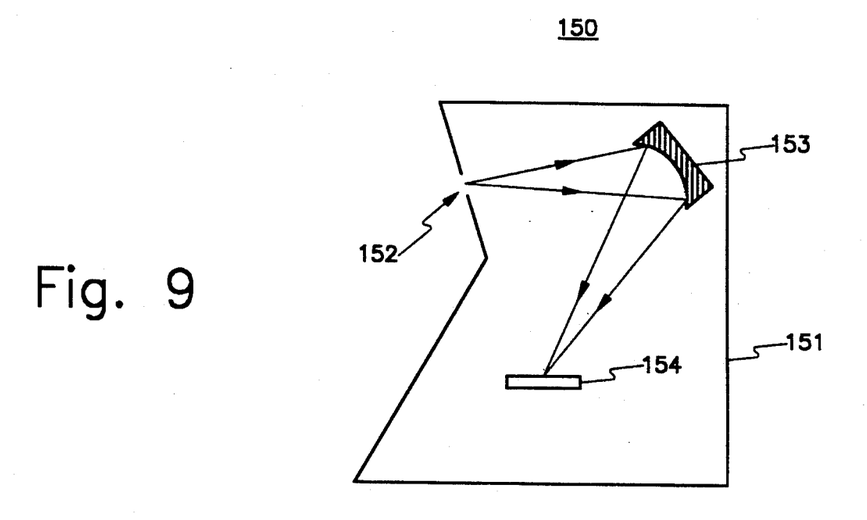
FIG. 9 is a cross-sectional, top view of the spectrograph of FIG. 8.

FIG. 8 shows a simplified view of spectrograph 150 which includes a housing 151, an entrance slit 152, a diffraction grating 153, and an optical detector 154. FIG. 9 shows a top cross-sectional view of spectrograph 150. Housing 151 is fabricated from cast aluminum for rigidity, strength, and integrity.

Diffraction grating 153 is a super aberration-corrected, concave, flat field, dispersive, holographic grating. Diffraction grating 153 has a plurality of grooves on its surface which are oriented parallel to entrance slit 152. Diffraction grating 153 serves two purposes. First, the grooves serve to diffract (or separate into individual wavelengths) the incoming light. Second, the concavity of the grating serves to focus the light on detector 154. In order to optimally perform these functions, diffraction grating 153 is fixed in a stationary position with respect to the focused, aligned, entrance slit 152.

Figure 10:
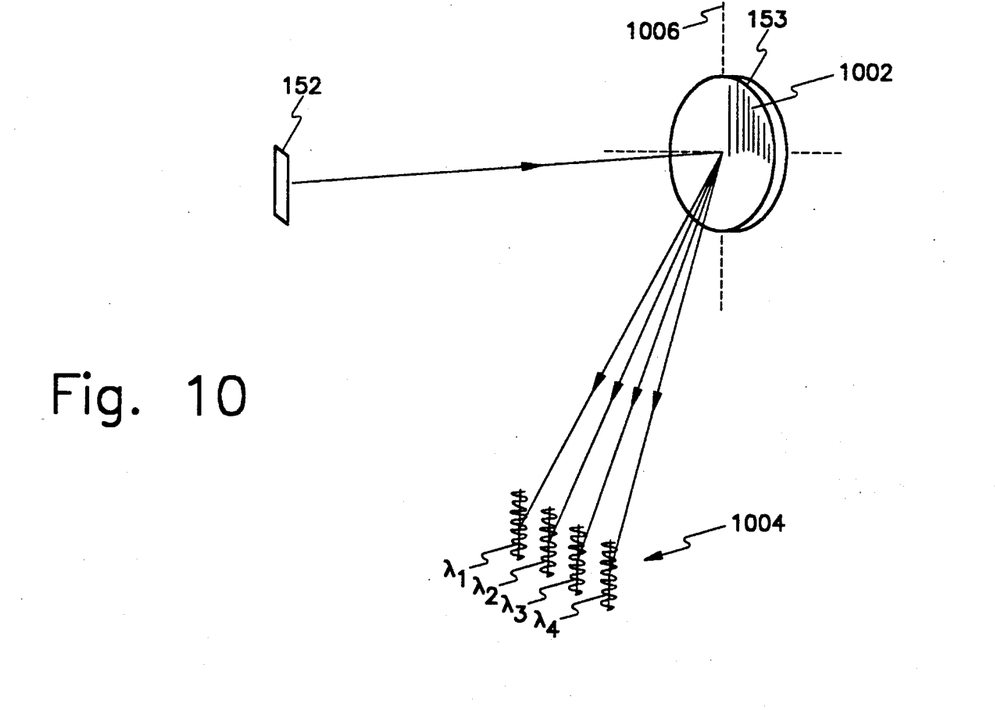
FIG. 10 is a diagram depicting the operational relationship between an entrance slit and a diffraction grating.

FIG. 10 illustrates operation of diffraction grating 153. Representative grooves 1002 are shown on grating 153 for illustration purposes. Grooves 1002 are parallel to an axis of diffraction 1006 of the diffraction grating. Polychromatic light incident upon diffraction grating 153 from entrance slit 152 is diffracted into a separated spectrum 1004. The different wavelengths of light in the spectrum 1004 are shown as spectral lines and are indicated as $\lambda_1$-$\lambda_4$. Note that entrance slit 152 is substantially parallel to grooves 1002 in grating 153.

Detector 154 is a linear array of photo-sensitive detector elements, such as silicon or InGaAs (Indium Gallium Arsenide) photodiodes or CCD's (charge coupled devices), which instantaneously converts light incident upon it into electrical signals. It is the finite number of elements available in known detector arrays which is responsible for the limited resolution of fixed grating analyzers. In other words, the greater the number of detector elements available in an array, the greater the analyzer's resolution will be.

Silicon detector arrays, which are currently available with as many as 4096 detector elements, provide the greatest resolution. Further, they provide performance which does not require cooling under most circumstances. However, silicon photodiodes are responsive to wavelengths in the range of 350 to 1100 nm (nanometers or $10^{-9}$ meters) and are thus not well suited for use in the NIR wavelength range.

For NIR applications, InGaAs photodiodes may be used. InGaAs detector arrays offer a wavelength responsivity of 800 to 1700 nm and are currently available with up to 256 elements. Because of the lessened number of elements, the InGaAs detector is capable of less resolution as compared with silicon. In the preferred embodiment, a 256 element InGaAs detector, model 1452 from Epitax, Inc. Princeton, N.J., is used for detector 154.

Although InGaAs detector arrays may be used at room temperature, optimum performance requires an efficient cooling scheme such as a two-stage Peltier (thermo-electric) cooling system.

Figure 11A:
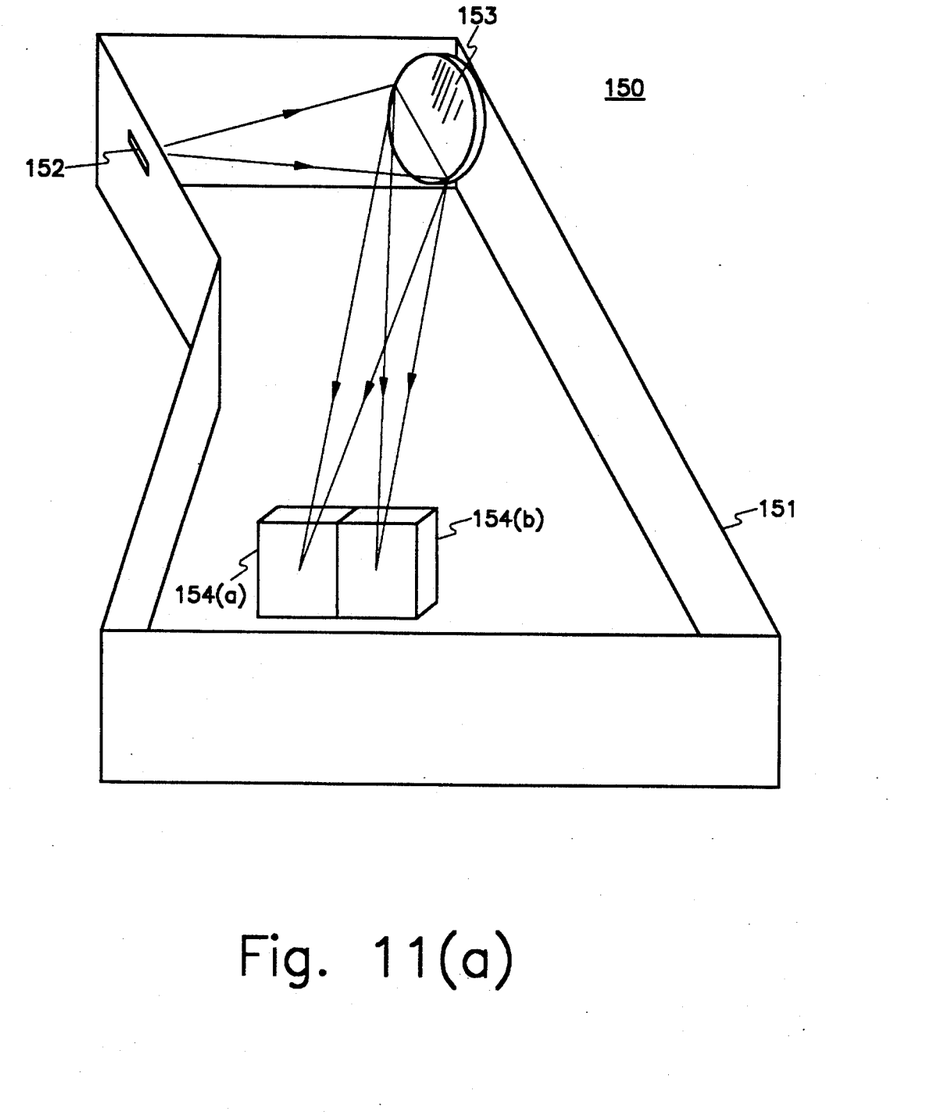
FIG. 11(a) is a simplified, perspective view of a detector array-type spectrograph using two detector arrays arranged in a side-by-side configuration.

It may be desirable to use more than a single detector array for detector 154. For example, two detector arrays may be placed in a side by side configuration as shown in FIG. 11(a) where detector 154 is implemented with a first detector array 154(a) and a second detector array 154(b). The same spectral energy from grating 153 will be incident across both of detector arrays 154(a) and 154(b). This scheme can be used to expand the wavelength range of detector 154.

By using detectors having different but slightly overlapping wavelength ranges, a wide bandwidth can be achieved and self calibration is possible. That is, measurements from the wavelength overlap spectrum of the two detector arrays can be compared and used to correct for detector measurement errors and wavelength range continuity. For example, a silicon detector array can be used for detector array 154(a) while an InGaAs detector array is used for detector array 154(b). Silicon and InGaAs have an overlap range of 800 to 1100 nm.

Figure 11B:
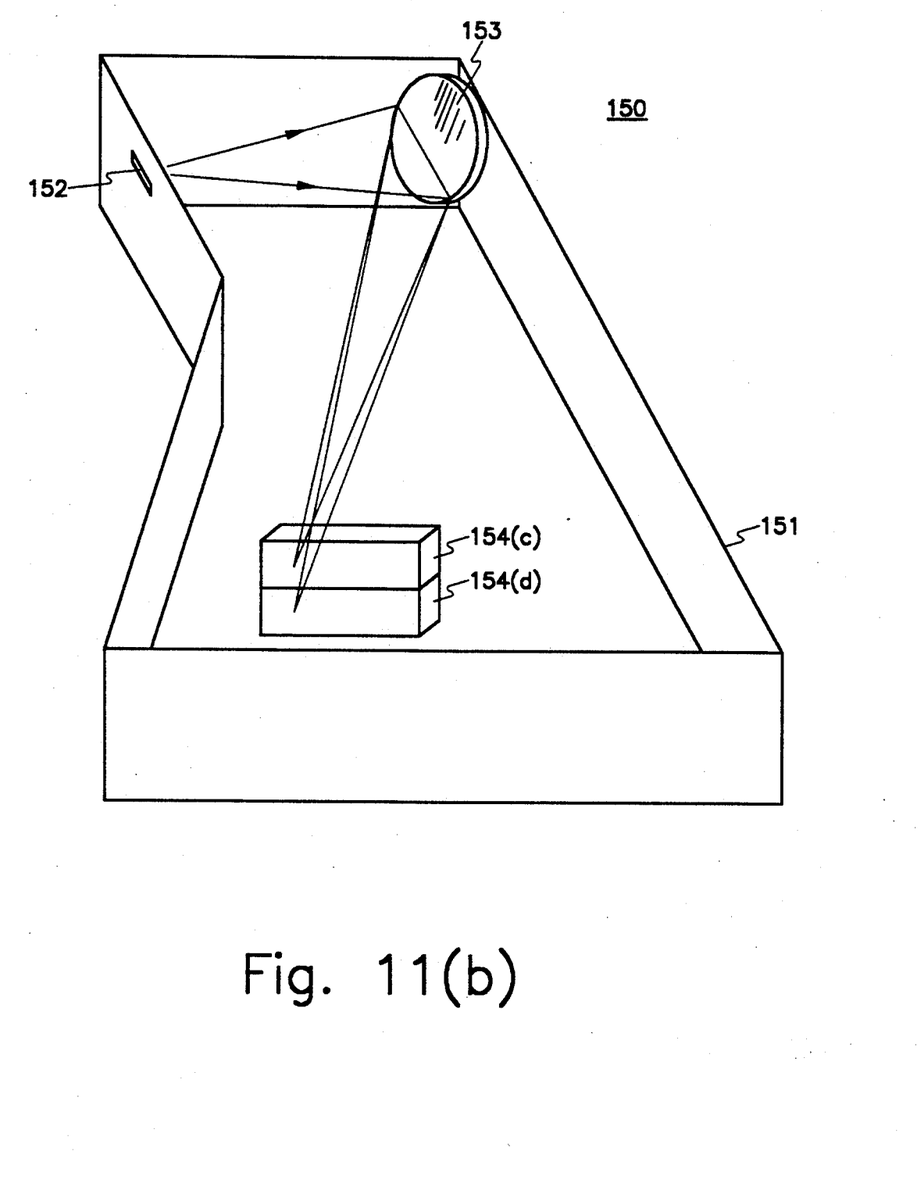
FIG. 11(b) is a simplified, perspective view of a detector array-type spectrograph using two detector arrays arranged in a stacked configuration.

Multiple detectors can also be oriented as shown in FIG. 11(b), where detector 154 is implemented with two detector arrays 154(c),154(d) in a stacked configuration. In this embodiment, certain wavelengths of the spectral energy from grating 153 will be incident on detector array 154(c) while other wavelengths are incident on detector array 154(d). This scheme can be used to increase the resolution of detector 154.

By spreading the diffracted spectrum of light over a larger detection area, the resolution of detector 154 is increased. Detector arrays 154(c) and 154(d) may be the same type of detector elements (e.g., InGaAs) or may be two different types of detector elements (e.g., silicon and InGaAs). Either way, an expanded wavelength range (as discussed above) and greater resolution results. Note, however, that no wavelength overlap exists in this embodiment for self calibration.

In the preferred embodiment, spectrograph 150 (not including slit array 140 or detector 154) is a conventional spectrograph part number CP-200, available from Instruments, S.A., Inc. of Edison, N.J.

Slit Array 140

The conventional entrance slit in spectrograph 150 is a mechanical opening which allows light to enter the spectrograph and fall incident upon the diffraction grating. FIGS. 8-11 show a conventional "parallel" entrance slit 152 for use with diffraction grating 153. The term "parallel" refers to the fact that the entrance slit is oriented parallel to axis of diffraction 1006 (see FIG. 10). The "axis of diffraction" is an imaginary axis runs through the center of the diffraction grating parallel to the grooves of the grating as described above.

When spectrograph 150 is used with optical fibers, the fibers are aligned to approximate, or correspond to, entrance slit 152. An actual physical entrance slit is not used. Rather, entrance slit 152 is replaced with an opening of whatever shape and size is required to couple the optical fibers to the spectrograph. The optical fibers approximate a physical slit opening as follows.

When used with a single optical fiber, the end of the fiber will be centered on the entrance slit. When several fibers are used to improve the intensity of a channel, they will be arranged in a line pattern corresponding to the slit opening. This is illustrated in the cross sectional end view of FIG. 12(a) for a parallel entrance slit configuration. Fiber pattern 1202 includes a row of eight fibers 1204. Axis of diffraction 1006 is superimposed on fiber pattern 1202 to show the parallel relationship therebetween.

This parallel arrangement of optical fibers (i.e. fiber pattern 1202) may also be used to implement multiple channels. That is, each optical fiber shown in FIG. 12(a) can represent a single channel. This parallel entrance slit arrangement of fibers results in "parallel multiplexing" or multiplexing parallel to the axis of diffraction. Note that MUX 130 performs the actual multiplexing. With this parallel orientation, each fiber, in turn, focuses its light on grating 153 to produce the desired spectrum on detector 154.

Unfortunately, parallel multiplexing cannot be used with more than a single fiber per channel. If more than one fiber per channel were used, then the additional fibers would have to be placed adjacent to the first fiber of each channel in a side-by-side configuration. This is illustrated by fibers 1203 which are shown in phantom in FIG. 12(a). Because the additional fibers are necessarily displaced from the axis of diffraction 1006, a spectral shifting results between the light from each fiber in the specific channel. This shifting causes the spectrum from one fiber to not correspond in position to the spectrum from a second fiber in the channel such that the resultant spectrum viewed at the detector will be corrupted. This corruption cannot be analytically corrected.

Figure 12:
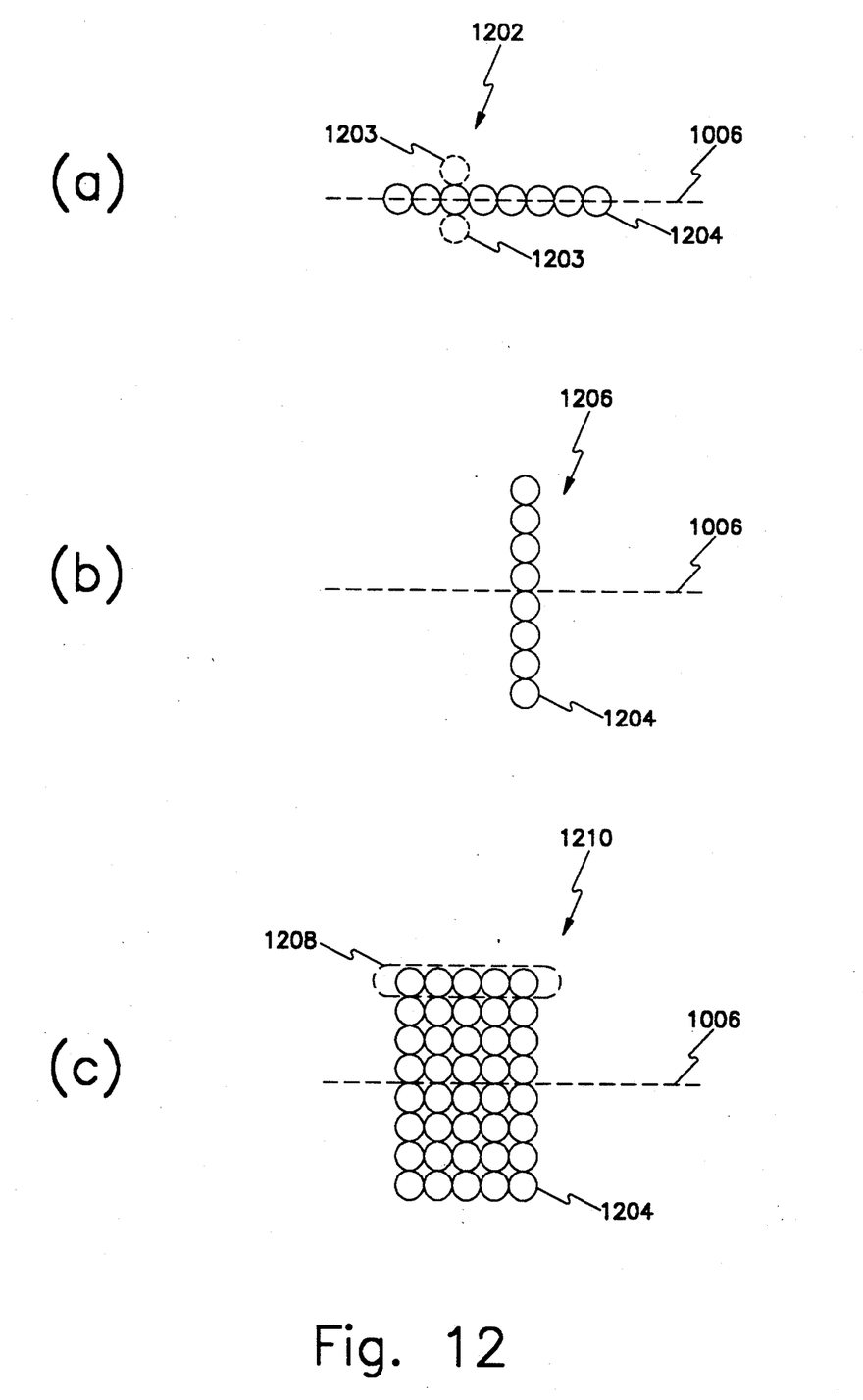
FIG. 12(a) is a cross-sectional end view illustrating the approximation of an entrance slit using optical fibers oriented along a line parallel to the axis of diffraction.
FIG. 12(b) is a cross-sectional end view illustrating the approximation of an entrance slit using optical fibers oriented along a line perpendicular to the axis of diffraction.
FIG. 12(c) is a cross-sectional end view illustrating an optical fiber arrangement of an entrance slit which allows multiple fibers and multiple channels to be used. Each horizontal row is an individual channel having multiple fibers.

For example, referring to FIG. 10, a first fiber horizontally centered in slit 152 will direct light onto grating 153 to produce the spectrum 1004 as shown. If a second fiber (carrying light having the same spectral contents as the first fiber) is stacked adjacent to the first fiber (as shown in FIG. 12(a)) then the angular orientation between the first fiber, the grating, and the detector will be different than the angular orientation between the second fiber, the grating, and the detector. This will cause the spectrum of the light from the second fiber and the spectrum of light from the first fiber to fall incident upon different portions of the detector. For example, a wavelength $\lambda_1$ of light from the first fiber may be centered on a central detector element of detector 154, while the same wavelength $\lambda_1$ of light from the second fiber is centered on a different diode in detector 154.

The inventors have discovered that this problem can be overcome by arranging the optical fibers in a "perpendicular multiplexing" scheme. That is, the fibers from each channel (forming a fiber optic entrance slit) are arranged in a pattern perpendicular to the axis of diffraction. This is illustrated in FIG. 12(b) where a single fiber per channel embodiment 1206 of a perpendicular entrance slit pattern is shown. Perpendicular entrance slit pattern 1206 includes a closely adjacent row of optical fibers 1204 which simulate a physical slit opening which is perpendicular to axis of diffraction 1006. Each fiber 1204 represents a single analyzer channel. The spectrum for each channel as seen by detector 154 will be spatially displaced with respect to all other channels due to the spectral shifting described above. Unlike the spectral shifting which occurs between the light from fibers of a single channel, however, this spectral shifting between different channels can be compensated for in analyzer electronics 170.

For a single fiber per channel slit array, there is no advantage in using perpendicular multiplexing as opposed to parallel multiplexing. However, perpendicular multiplexing allows the use of multiple fibers per channel. This is illustrated in the example of FIG. 12(c). Slit array 1210 includes forty fibers. That is, eight channels, each containing five fibers arranged in a line parallel to axis of diffraction 1006, are perpendicularly multiplexed as described above. For example, a first channel 1208 has five fibers aligned parallel to the axis of diffraction.

Note that in the perpendicular multiplexing of multi-fiber channels, the light from each fiber in a channel will produce a coincident spectrum on detector 154. It is only the light from different channels that will be spectrally shifted. This however is not a problem because only a single channel is ever active at any one time. As discussed above, this spectral shifting between different channels can be compensated for in analyzer electronics 170.

If, as suggested above, optical fibers 164 are replaced with waveguides, then slit array 140 could also be formed using waveguides.

Analyzer Electronics 170

Figure 13:
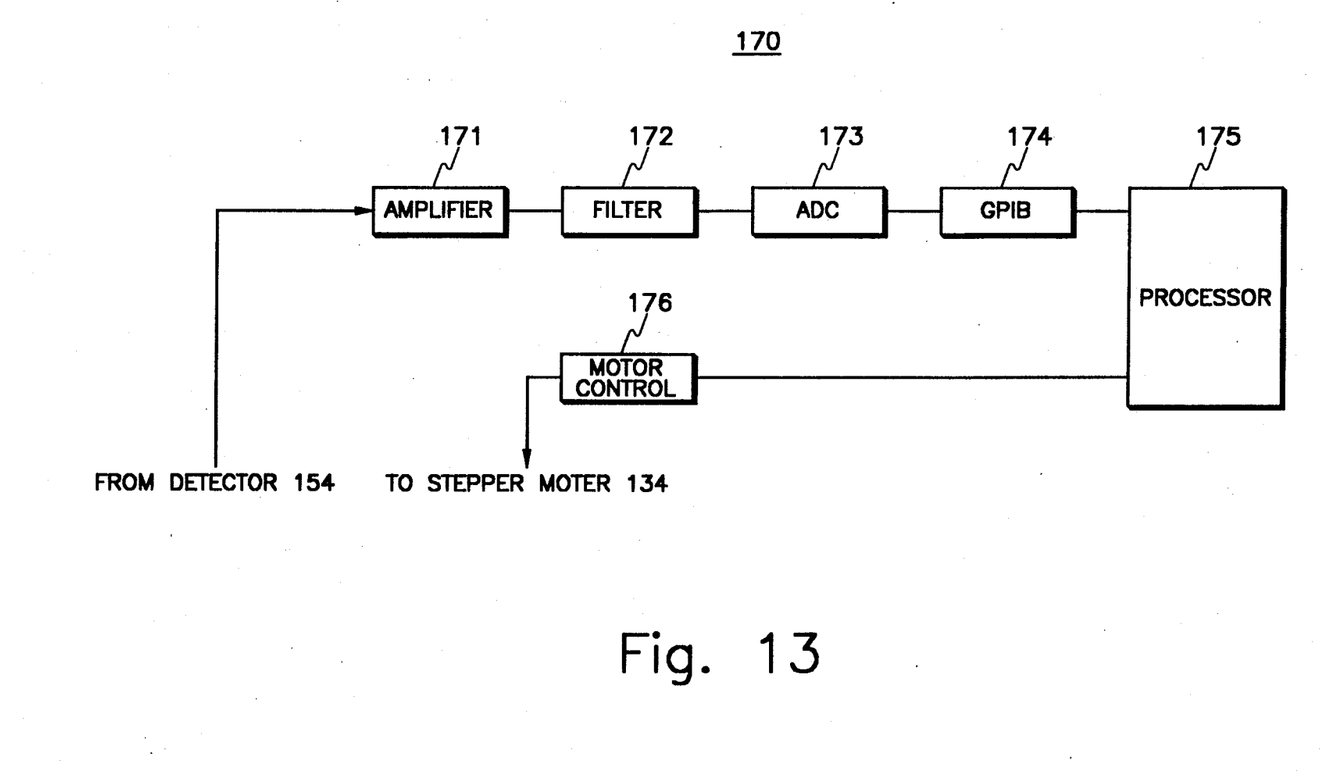
FIG. 13 is a block diagram of analyzer electronics 170.

Referring now to FIG. 13, analyzer electronics 170 includes: a detector preamplifier 171, a filter circuit 172, an analog-to-digital converter (ADC) 173, a general purpose interface bus (GPIB) 174, a digital signal processor 175, and a motor controller 176. Detector preamplifier 171 receives, from detector 154, electrical signals which are representative of the optical spectrum of a sample and amplifies these signal. The amplified signal is then filtered in a low-pass filter 172 to remove noise prior to being digitized in ADC 173. The digital signal representing a sample spectrum is then transmitted to processor 175 over GPIB 174.

The rate at which ADC 173 can digitize a signal and the sampling resolution are the controlling factors which limit the scan and processing speed of analyzer 100. Thus, it is important that a very quick device be selected for ADC 173. There is a design trade-off made between sampling resolution (the number of elements in detector array 154 and the sampling interval of ADC 173) and scan rate or speed. In the preferred embodiment, preamplifier 171, filter 172, and ADC 173 may be purchased as a single unit. The unit, called a "diode array instrument", part number 1471A, is available from EG&G Park, Inc. of Princeton, N.J.

GPIB 174 is an IEEE-488 standard high-speed, parallel data interface bus. In the preferred embodiment, data can be transmitted from amplifier 171 to processor 175 (over GPIB 174) at rates exceeding 500 KiloBytes per second.

Processor 175 is the integrator of all the electronics and provides data analysis and control for analyzer 100. Processor 175 is a floating point digital signal processing microcomputer capable of providing the high speed clocking and control for the other electronics, and having the computational power to perform millions of floating point operation in a second. In the preferred embodiment, processor 175 is a general purpose microcomputer equipped, for example, with a 8386 processor and a digital signal processing board. Alternatively, processor 175 may be implemented with dedicated hardware.

Motor controller 176 includes driver circuitry for controlling stepper motor 134 in MUX 130. Motor controller 176 is controlled directly by processor 175.

Software

The application software which runs on processor 175 may be divided into four distinct portions. A first portion provides a user interface and controls overall operation of analyzer 100. A second portion is used for spectral modelling. A third portion performs continuous data analysis. Finally, the fourth portion controls data output.

Spectral modelling is performed by LightCal 1.20, which is a product of LT Industries, Inc. of Rockville, Md. This program uses chemometrics to perform spectral identification. Chemometrics are algorithmic techniques that convert spectral information into analyses that identify the presence and concentration of the constituents of a sample. These techniques allow adaptive analyses that include such features as bad scan rejection, bubble detection in liquid streams, and confidence estimations. The application of chemometrics to spectral analysis allows a scientific instrument requiring human interpretation to become a self-sufficient analyzer capable of reliable, unattended analyses.

The continuous analysis software uses the models produced by the modelling software to perform that actual constituent concentration predictions. The data output software produces sample data in a user friendly format. In the preferred embodiment, data output provides spectral graphs for each sample.

Spectral Calibration and Wavelength Drift Compensation

Spectral calibration and wavelength drift compensation are performed according to the method set forth in U.S. Pat. No. 5,020,909, titled "AN 'INLINE' SPECTRAL REFERENCE METHOD FOR SPECTROMETERS", which is incorporated herein by reference. Essentially, MUX 130 can provide five different situations to spectrograph 150. These include:

(1) light from a sample (e.g., one of channels 1–7) is passed through the air gap of opening 139(1) of MUX 130;
(2) light from a sample is passed through the reference material of opening 139(2) of MUX 130;
(3) black or no light is passed through opening 139(3) of MUX 130;
(4) white or light directly from light source 110 is passed through the air gap of opening 139(1) of MUX 130 via fiber bundle 160(8); and
(5) reference white or light directly from light source 110 is passed through the reference material of opening 139(2) of MUX 130 via fiber bundle 160(8).

In situation (1), processor 175 is presented with a spectrum of the sample (i.e., "sample spectrum") and spectral changes introduced by analyzer 100 itself (i.e., "instrument spectrum"). The instrument spectrum includes the optical characteristics of the analyzer optics and detector 154, errors introduced by analyzer electronics 170, and drift errors caused by lamp variations, electronic component variations, and electronic noise.

In situation (2), processor 175 is presented with a sample spectrum, an instrument spectrum, and a "reference spectrum". The reference spectrum is the spectrum of the reference material found in opening 139(2) of MUX 130. The reference material is largely transparent and has a predetermined distincitive and stable absorption spectrum which can be used for calibration. In the preferred embodiment, polystyrene is used. Other reference materials, such as Holmium glass, and other National Bureau of Standards traceable standards could also be used.

Passing light through the reference material causes the spectrum of the incident light to be convoluted with the absorption spectrum of the reference material.

In situation (3), no light is allowed to pass through MUX 130. Thus, only portions of the instrument response will reach processor 175. These portions include electronic drift and noise.

In situation (4), the light from source 110 is routed directly to spectrograph 150 through MUX 130. This will present an instrument spectrum to processor 175.

In situation (5), the light from source 110 is routed to spectrograph 150 through the reference material in MUX 130. This will present both an instrument spectrum and a reference spectrum to processor 175.

The information provided by these various combinations of spectra can be used by processor 175 to calibrate each channel of analyzer 100 such that absorption spectrum of a sample can be accurately determined. Calibration proceeds as follows:

1. a channel of analyzer 100 is selected for calibration;
2. chopping disk 132 of MUX 130 is rotated so that air gap of opening 139(1) is placed in line with the selected channel;
3. light from light source 110 is passed through or made incident on a sample (by a probe 120) to be analyzed, the light reflected from or transmitted through the sample is then collected (by probe 120) and routed through optical MUX 130 to slit array 140, slit array 140 introduces the light into spectrograph 150 from a fixed point where it falls incident upon grating 153 and is diffracted onto detector 154;
4. the spectrum of the sample (sample spectrum) which is convoluted with the instrument spectrum is detected by detector 154 and recorded in memory by processor 175;
5. chopping disk 132 of MUX 130 is rotated so that the reference material in opening 139(2) is place in line with the selected channel;
6. step 3 is repeated;
7. the sample spectrum which is convoluted with the instrument spectrum and the reference spectrum is detected by detector 154 and recorded in memory by processor 175;
8. the sample and instrument spectra (step 4) are subtracted from the sample, instrument, and reference spectra (step 7) by processor 175 to yield a measured reference spectrum;
9. the measured reference spectrum (step 8) is compared to an actual reference spectrum to determine the spectral distortion introduced by the selected channel of analyzer 100 and to determine the offset introduced by the perpendicular multiplexing of channels performed by slit array 140;
10. spectral correction data is produced for the selected channel based on the comparison of step 9;
11. repeat steps 1–9 for each channel of analyzer 100;

In addition to these steps set forth above, two further steps may be used in performing an initial calibration of analyzer 100. These include a step of passing light from light source 110 directly into spectrograph 150 via optical fiber bundle 160(8). This will present an instrument spectrum to detector 154. The other additional step includes rotating chopping wheel 132 such that opening 139(3) is aligned with a MUX channel. This blocks light from all channels such that no light reaches spectrograph 150 and analyzer electronics 170 is presented only with the electronic drift and noise portion of the instrument spectrum as described above. The spectral information from these two additional steps may be used to isolate spectral error sources in analyzer 100.

Chief among the advantages of this approach is that a dedicated optical beam for reference is not required. In addition, the entire optical system, including the sample and sampling accessories, are included directly in the calibration and compensation loop. The result of this method is a corrected, absolute spectrum of a sample with total compensation for intensity drifts, wavelength shifts, and other spectral distortions.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those of skill in the art.

We claim:

1. An apparatus for optically analyzing a plurality of samples, the apparatus comprising:
   (a) light source means for generating a source light having a preselected spectrum of wavelengths;
   (b) spectrograph means for receiving incident light and for separating said incident light into individual wavelengths for analysis, said spectrograph means including a light entrance, a diffraction grating and an optical detector, said detector producing an electrical signal representative of the spectral contents of said incident light;
   (c) optical multiplexing means having a plurality of multiplexer channels for the selective transmission of incident light through one multiplexer channel at a time, each said multiplexer channel including an input opening for receiving said incident light and an output opening for transmitting said incident light; and
   (d) a plurality of analysis channels, each analysis channel including:
      (i) optical probe means adapted to receive said source light, to focus said source light on a sample material to produce a sample convoluted light, and to collect said sample convoluted light;
      (ii) first optical interconnect means for guiding said source light from said source means to said optical probe means;
      (iii) second optical interconnect means for guiding said sample convoluted light from said optical probe means to one of said multiplexer channels; and
      (iv) third optical interconnect means for guiding said sample convoluted light from said one of said multiplexer channels to said light entrance of said spectrograph means, said third optical interconnect means having a first end and a second end, said first end being connected to said output opening of said multiplexer channel;
   said second ends of said third optical interconnect means of said plurality of analysis channels being arranged to form an entrance slit array, said entrance slit array being coupled to said light entrance of said spectrograph means for focusing said sample convoluted light on said diffraction grating.

2. The apparatus of claim 1, wherein said first, second, and third optical interconnect means each comprise a single optical fiber.

3. The apparatus of claim 2, wherein said entrance slit array is formed by arranging said second ends of said third optical interconnect means of said plurality of analysis channels in a line parallel to an axis of diffraction of said diffraction grating.

4. The apparatus of claim 2, wherein said entrance slit array is formed by arranging said second ends of said third optical interconnect means of said plurality of analysis channels in a line perpendicular to an axis of diffraction of said diffraction grating.

5. The apparatus of claim 4, wherein said optical multiplexing means is operable, for each multiplexer channel, to selectively convolute said sample convoluted light with a reference spectrum.

6. The apparatus of claim 5, further comprising:
   (e) electronic means for receiving said electrical signal from said optical detector and for determining the spectral composition of light incident upon said optical detector therefrom.

7. The apparatus of claim 1, wherein said first, second, and third optical interconnect means each comprise a plurality of optical fibers.

8. The apparatus of claim 7, wherein said second end of said third optical interconnect means of each analysis channel are arranged in a line parallel to an axis of diffraction of said diffraction grating to form a single channel slit pattern, and wherein said entrance slit array is formed by arranging said single channel slit patterns for said plurality of analysis channels into a matrix along a line perpendicular to said axis of diffraction.

9. The apparatus of claim 8, wherein said optical multiplexing means is operable, for each multiplexer channel, to selectively convolute said sample convoluted light with a reference spectrum.

10. The apparatus of claim 9, further comprising:
    (e) electronic means for receiving said electrical signal from said optical detector and for determining the spectral composition of said incident light therefrom.

11. An apparatus for optically analyzing a plurality of samples, the apparatus comprising:
    (a) a light source;
    (b) a spectrograph including a light entrance, a diffraction grating and an optical detector;
    (c) an optical multiplexer having a plurality of multiplexer channels for the selective transmission of incident light through one multiplexer channel at a time, each said multiplexer channel including an input opening for receiving said incident light and an output opening for transmitting said incident light; and
    (d) a plurality of analysis channels, each analysis channel including:
       (i) an optical probe adapted to receive said source light, to focus said source light on a sample material to produce a sample convoluted light, and to collect said sample convoluted light;
       (ii) first optical interconnect means for guiding said source light to said optical probe;
       (iii) second optical interconnect means for guiding said sample convoluted light from said optical probe to one of said multiplexer channels; and
       (iv) third optical interconnect means for guiding said sample convoluted light from said one of said multiplexer channels to said light entrance of said spectrograph, said third optical interconnect means having a first end and a second end, said first end being connected to said output opening of said multiplexer channel;
    said second ends of said third optical interconnect means of said plurality of analysis channels being arranged to form an entrance slit array, said entrance slit array being coupled to said light entrance of said spectrograph for focusing said sample convoluted light on said diffraction grating.

12. The apparatus of claim 11, wherein said first, second, and third optical interconnect means each comprise a plurality of optical fibers.

13. The apparatus of claim 12, wherein said second end of said third optical interconnect means of each analysis channel are arranged in a line parallel to an axis of diffraction of said diffraction grating to form a single channel slit pattern, and wherein said entrance slit array is formed by arranging said single channel slit patterns for said plurality of analysis channels into a matrix along a line perpendicular to said axis of diffraction.

14. The apparatus of claim 13, wherein said optical multiplexer is operable, for each multiplexer channel, to selectively convolute said sample convoluted light with a reference spectrum.

* * * * *